United States Patent
Cejnar

(10) Patent No.: US 8,958,878 B2
(45) Date of Patent: Feb. 17, 2015

(54) LOW PROFILE ADAPTER FOR CONTINUOUS CONNECTION OF PACEMAKER LEAD DURING IMPLANTATION

(76) Inventor: Michael Cejnar, Sydney (AU)

( * ) Notice: Subject to any disclaimer, the term of this patent is extended or adjusted under 35 U.S.C. 154(b) by 287 days.

(21) Appl. No.: 12/807,957

(22) Filed: Sep. 17, 2010

(65) Prior Publication Data

US 2012/0071945 A1    Mar. 22, 2012

(51) Int. Cl.
*A61N 1/05* (2006.01)
*A61N 1/372* (2006.01)
*A61N 1/375* (2006.01)
*H01R 11/22* (2006.01)
*H01R 24/58* (2011.01)

(52) U.S. Cl.
CPC ............. *A61N 1/056* (2013.01); *A61N 1/37241* (2013.01); *A61N 1/3752* (2013.01); *H01R 11/22* (2013.01); *H01R 24/58* (2013.01); *H01R 2201/12* (2013.01); *H01R 2201/20* (2013.01)
USPC .......................................................... 607/37

(58) Field of Classification Search
USPC ....................... 607/10, 37, 116, 119, 122, 123
See application file for complete search history.

(56) References Cited

U.S. PATENT DOCUMENTS

| | | | |
|---|---|---|---|
| 4,951,687 A | 8/1990 | Ufford et al. | |
| 5,782,892 A | 7/1998 | Castle et al. | |
| 6,038,481 A | 3/2000 | Werner et al. | |
| 6,363,288 B1 | 3/2002 | Bush et al. | |
| 6,799,991 B2 | 10/2004 | Williams et al. | |
| 6,921,295 B2 | 7/2005 | Sommer et al. | |
| 7,225,034 B2 | 5/2007 | Ries et al. | |
| 7,753,696 B2 | 7/2010 | Hoecke et al. | |
| 2002/0116035 A1* | 8/2002 | Klehn | 607/37 |
| 2003/0120327 A1 | 6/2003 | Tobritzhofer et al. | |
| 2005/0177199 A1* | 8/2005 | Hansen et al. | 607/37 |
| 2011/0160817 A1* | 6/2011 | Foster et al. | 607/116 |
| 2011/0160824 A1 | 6/2011 | Ware et al. | |

* cited by examiner

*Primary Examiner* — Carl H Layno
*Assistant Examiner* — Jon Eric C Morales

(57) ABSTRACT

A low profile electrical adapter body releasably connects to the electrodes of a pacing lead connector, such as an IS-1. Spring steel lead connector holders and the twist-tolerant cable allow continuous ECG recording while manipulating the pacing lead. The adapter body includes two lead connector holders. A grip longitudinally aligns the lead connector within the adapter body. The grip is slidably attached to a twist-tolerant cable and releasably engages the adapter to form a single adapter assembly that enlarges the device for easier digital manipulation. A twist-tolerant cable connects the low profile adapter directly or indirectly to a medical test device such as a pacemaker analyzer.

7 Claims, 5 Drawing Sheets

LOW PROFILE ADAPTER FOR CONTINUOUS CONNECTION OF PACEMAKER LEAD DURING IMPLANTATION

FIELD OF THE INVENTION

The invention relates to a low-profile adapter for the temporary, uninterrupted electrical connection of a test device, such as a pacemaker analyzer, to an implantable cardiac pacemaker lead during its manipulation by the implanting surgeon.

BACKGROUND OF THE INVENTION

The Pacemaker-Lead System

When the heart fails to beat or beats irregularly, physicians may implant a pacemaker to ensure the regular beat of the heart. Pacemakers have implantable electrical leads, i.e., specially coated wires with electrodes at the tip that connect the pacemaker to the heart, usually to its inner wall via the venous system. FIG. 1 depicts a pacemaker 10 and an implantable lead 20. The pacemaker senses electrical activity and sends an electrical current through the implantable lead to the heart at appropriate intervals to regulate the heartbeat. The distal (i.e., most distant from the pacemaker) end 24 of the lead 20 is located typically on the endocardium of the heart. The proximal (i.e., closest to the pacemaker) end 22 of the lead 20 generally has a single or multiple coaxial contact assembly for insertion into and electrical coupling with pacemaker 10.

Description of the Lead

Implantable leads have one or more distal "electrodes", which are metallic contact surfaces for transmitting electrical signals into and from the heart tissue. One example of an electrode is distal end 24 of implantable lead 20 in FIG. 1. In an implantable lead, each electrode is attached to a unique contact (not shown) in lead connector 22 in FIG. 1. The number of electrode-contact circuits is also referred to as the number of "poles" the lead has. A stylet or a removable stiff wire 110 (see FIG. 4) may be inserted into a central channel spanning the entire length of the pacing lead to stiffen the lead to facilitate its manipulation in the body.

Implantable leads have distal ends that are a) passively fixated, using "tines" or tiny wings that entangle with cardiac structures on the inside of the heart, or b) actively fixated, where the distal tip electrode consists of a corkscrew which is twisted out of the barrel of the distal lead and into the heart tissue. FIG. 1 depicts the wings of a passively fixated tip 24. Leads may be either unipolar, having just one distal tip electrode, or bipolar, with one tip electrode and a second ring electrode located on the lead shaft about 3-10 mm from the tip. Specialized leads may have 3 or more electrodes.

The IS-1 connector is currently the industry standard 3.2 mm, in-line, two-contact electrical connector. The IS-1 standard is defined by ISO 5841-3:1992, Rev 2000, Cardiac pacemakers—Part 3: Low-profile connectors (IS-1) for implantable pacemakers. An example IS-1 can be seen in FIG. 3. Proximal end 31 of IS-1 co-axial bipolar connector 30 has two electrodes 32, 34 and two sets of silicon sealing rings 33, 35. In an actively fixated lead, a tiny torque wrench fits the most proximal contact on the IS-1 connector 30. When turned, the wrench rotates the distal corkscrew electrode via a torquable conductor within the body of the lead. Typically 8 to 12 full turns are required to engage the corkscrew electrode.

Implanting the Lead

Implantation of pacing leads typically involves the insertion of the lead through a peripheral vein into the heart under X-ray fluoroscopic guidance and manipulation of the lead around the heart until a suitable permanent location is found. Indicators of adequate location include the anatomical location, the stability of the lead as it appears on the fluoroscope, and electrical characteristics, including adequate sensing of cardiac electrical activity at the site and a low pacing threshold, which is the minimum stimulating current necessary to contract the heart. Some of these indicators are determined by a pacemaker analyzer, such as the Medtronic PSA 5311. FIG. 4, while depicting certain aspects of the present invention, also generally represents a pacemaker analyzer 196 electrically connected to a pacing lead 120. Manipulation of the lead requires a continuing series of push-pull movements, flexing, and multiple full axial rotations of the lead.

Prior Art

To electrically test the pacing lead's position, the prior art uses a relatively stiff speaker wire lead 70, 71 terminated by alligator clips 42 and 44 (see FIG. 2) to connect from the pacemaker analyzer to the contacts on the lead connector (see FIG. 3). The stiff cable and its bulky alligator clips do not readily allow manipulation of the lead while the clips are connected. This necessitates electrically "blind" manipulation of the lead with numerous iterations of lead manipulation without electrical feedback from the analyzer. Typically the lead is manipulated without the alligator clips connected. To measure the electrical quality of current particular pacing site the physician stops manipulating the lead, connects the alligator clips, and then measures the site quality. To resume testing additional sites the physician disconnects the alligator clips, manipulates the lead to another site without electrical feedback from the analyzer, stops manipulation, reconnects the alligator clips, etc.

Historically, pacing leads were typically placed into the relatively easy implant sites of the right ventricular apex and the right atrial appendage. Under these circumstances blind manipulation of the lead was tolerable, usually requiring only a limited number of connections and disconnections of the alligator clips and taking only 15 to 45 minutes. Failed lead implantations were rare. In the last 5 to 10 years, physicians have been implanting pacing leads in new and more difficult cardiac locations for more physiological pacing and to resynchronize cardiac contraction in heart failure. This approach has generally improved long term cardiac function. New pacing lead locations currently include the left cardiac veins, right ventricular septum or outflow tract, atrial septum, adjacent to His Bundle, in Bachman's bundle and inside Coronary Sinus, as well as on the epicardium. Finding the optimal pacing lead site has thus become far more challenging and time consuming, requiring numerous relocations of the lead and thus repeated testing using the alligator clips, with implant procedures taking 1.5 to 2 hours to complete, sometimes far longer and with not infrequent failures to secure an adequate pacing site.

This need for connection and reconnection is a disadvantage because it results in only intermittent testing of possible lead positions, adds to procedure time, distracts the physician from manipulation of the lead, may delay or even prevent the identification of the optimal pacing site, and adds to the risk of contamination of the lead and thus infection. Secondary unfavorable effects from prolonged implant procedures include an increase in operator fatigue, greater risk to the patient from anesthesia-related complications, higher cost per procedure, and higher risk of trauma, including heart perforation.

The prior art in lead adapters reflects attempts to allow compatibility of connection to various lead connector geometries or to improve security of lead connection, but none address safety and manipulability of the connected lead during implantation. A typical coaxial pacing lead IS-1 connector to which this invention may connect is described in U.S. Pat. No. 4,951,687. U.S. Pat. No. 6,038,481 to Werner et al describes a lead adapter between pacing leads and a pacemaker analyzer but the adapter is too large, heavy and cumbersome to allow lead manipulation that involves multiple rotations of the lead and connector. The Werner et al design also does not accommodate the small torque wrench required for actively fixated leads. Furthermore, Werner et al teaches securing the adaptor to the connector. U.S. Pat. No. 5,782,892 depicts a large lead adapter designed to securely accommodate different lead connector geometries but which is unsuitable to manipulation of the lead. U.S. patent application No. 2003/0120327 depicts a simpler, smaller adapter but is designed for connection to temporary pacing leads with different connectors to those of permanent leads and not suitable for manipulation of the leads. U.S. Pat. No. 6,921,295 describes a large complex adapter to join, upsize, and adapt leads with different connector geometries. It is unsuitable for manipulation during implantation.

In view of the current state of the art, it is desirable to have a pacing lead adapter that remains connected to the lead during manipulation of the lead to provide continuous measurement of lead parameters. This same adapter, however, must disconnect readily if required by the physician and in case of inadvertent pull on the adapter to prevent potentially lethal tearing of the lead out of the heart, especially in the case of an actively fixated lead. Such an adapter would need to be small, light, and have a low profile above the lead, and its connecting cable should be light and pliable enough so that the physician can hold the pacing lead in his hands and push, pull, move and twist the lead many times without any impediment from the adapter or its attached cable. Furthermore, the cable between the adapter and the pacemaker analyzer should also be compliant and twist-tolerant so as to not inhibit the rotation, twisting and bending of the pacing lead during its manipulation.

SUMMARY OF THE INVENTION

With today's increasing demands on cardiologists to locate pacing leads in diverse and challenging cardiac sites, the present invention provides the much-needed constant feedback during continuous manipulation, which the prior art does not have. The invention will allow shorter implant time, optimize lead locations that will in turn improve lead parameter values, reduce trauma to the heart, and lower the associated procedure risks and costs.

The preferred embodiment of the invention includes: (i) a low-profile, light-weight adapter assembly with two spring clip contacts for releasably holding the two contacts of a pacing lead connector such as the IS-1; (ii) the most proximal spring clip contact is preferably disposed at or near one end of the adapter body and is narrow enough to provide room on the lead connector's proximal electrode for a small torque wrench to rotate the lead connector in the case of actively fixated leads; (iii) a grip, removably engageable with the adapter body, with guides and a central slot for the pacing lead stylet to aid the physician to precisely locate the adapter onto the pacing lead connector; (iv) the proximal clip contact is designed such that it exerts sufficient force to make good electrical contact with the pacing lead connector contact, while allowing for the normal and intended functioning of the pacing lead, i.e., rotation of the lead connector contact; (v) a long, pliable twist-tolerant connection cable for connecting the adapter to the pacemaker analyzer; and, (vi) two electrical receptacles located on the pacemaker analyzer end of the adapter connecting cable that can connect to the industry standard two alligator clips used in all of the various proprietary pacemaker analyzer connecting cables, or alternatively, a specific electrical plug for connection into specific pacemaker analyzers.

The clip contacts preferably have a controlled spring force to ensure the adapter does not readily lose electrical connection from the pacemaker analyzer during manipulation. At the same time the clips' spring force is limited and size and geometry, so designed that the lead connector will disengage from the pacemaker lead if the connector cable is accidentally pulled. This is important, because an accidental force on or rapid extraction of the lead, especially an actively fixated lead, may damage cardiac structures or even cause a potentially lethal tear in the heart.

The removable grip engages the tiny adapter body to form a single, larger assembly for easier handling with the fingers and locates the adapter's clip contacts precisely and effortlessly onto the lead connector contacts and sealing rings. In a preferred embodiment of the invention the removable grip, once removed, slides back along the twist-tolerant connecting cable but cannot be removed from the cable. This prevents the grip from getting lost in case it is needed again. Also, this configuration prevents the grip from falling into an open wound, or from being inadvertently left behind in the wound.

The present invention has numerous advantages over the prior art. It allows continuous measurement of intracardiac electrocardiogram (IECG) signals and pacing thresholds during manipulation of the lead. It improves the likelihood that the physician will locate the optimal pacing site. It eliminates the need to maneuver alligator clips on and off the lead connector numerous times during implantation, thus further reducing procedure time. The invention connects the lead connector's electrodes precisely, securely, and with controlled high-quality contact, reducing the chance of a bad connection, loss of the connection, or induced noise from an intermittent connection. The contacts further reduce the potential for damage to the lead connector, especially the soft sealing rings, by the alligator clips. In addition, the absence of repeated connections and disconnections reduces the chance for contamination of the lead connector, which in turn reduces the possibility of infection. Earlier procedural success also reduces the potential for damage to or perforation of the myocardium from prolonged manipulation of the lead inside the heart.

BRIEF DESCRIPTION OF THE DRAWINGS

The features and elements characteristic of the invention are described below and set forth in the appended claims. The figures are for illustration purposes only and are not drawn to scale. The invention itself, however, both as to its structure and method of operation, may best be understood by reference to the detailed description which follows and the knowledge of those skilled in the art, taken in conjunction with the accompanying drawings in which:

DETAILED DESCRIPTION OF THE PREFERRED EMBODIMENTS

The Adapter Body, the Grip, and the Adapter Assembly

Figure 4:
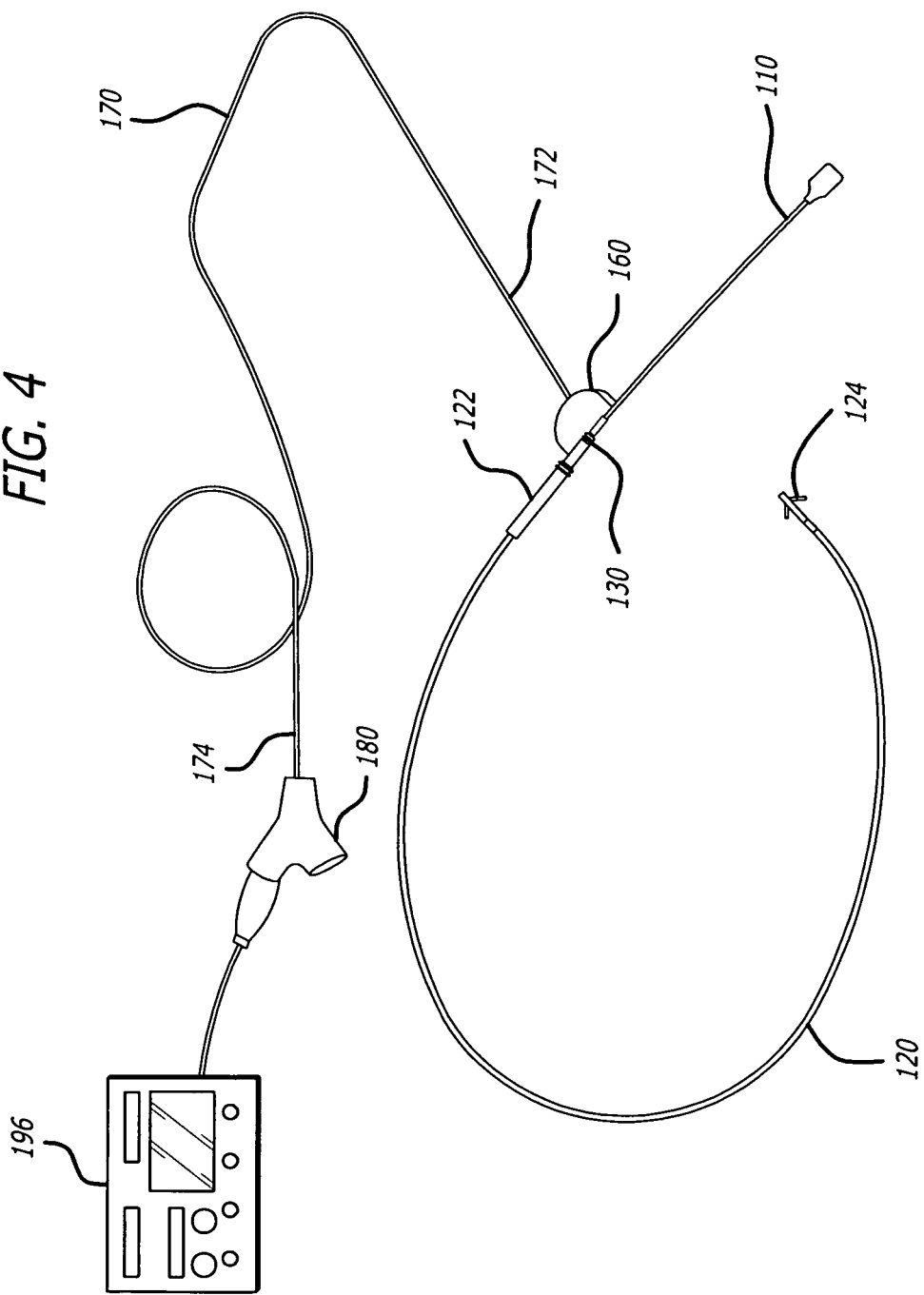
FIG. 4 is a view of the present invention connected to an implantable lead at the distal end and to an electrical device at the proximal end.
Figure 5:
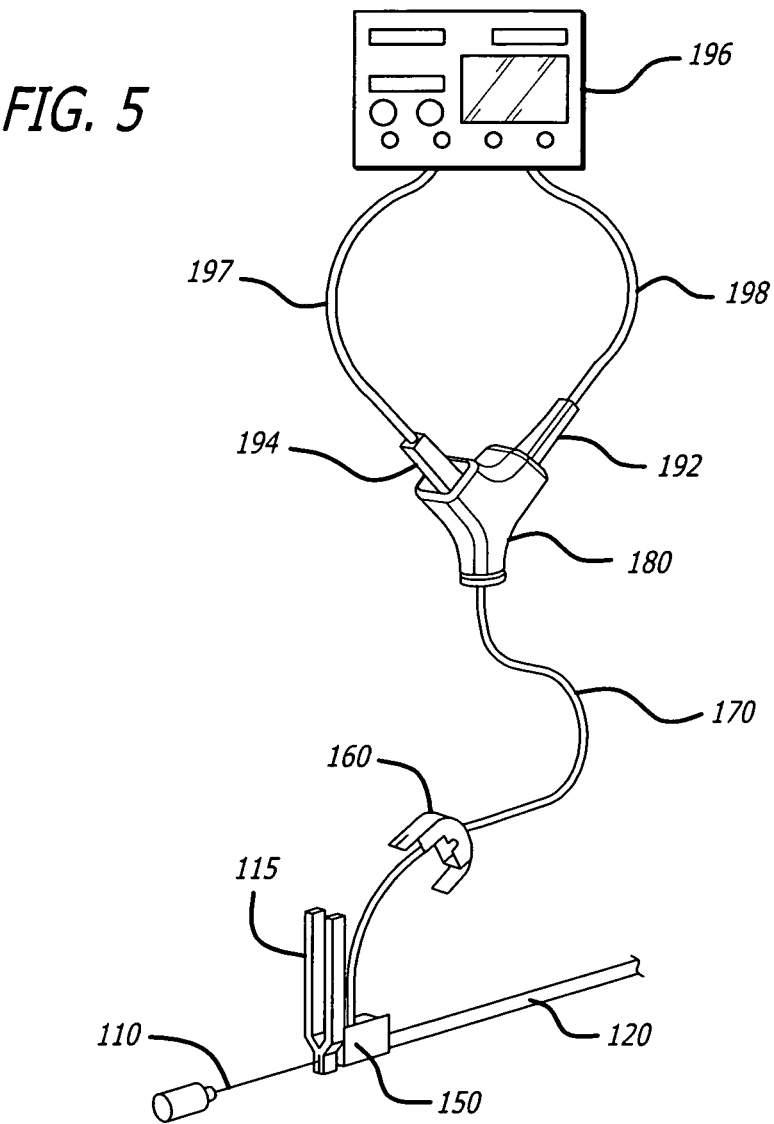
FIG. 5 is an exploded view of the invention with the grip and adapter engaging each other to form a single assembly.
Figure 6:
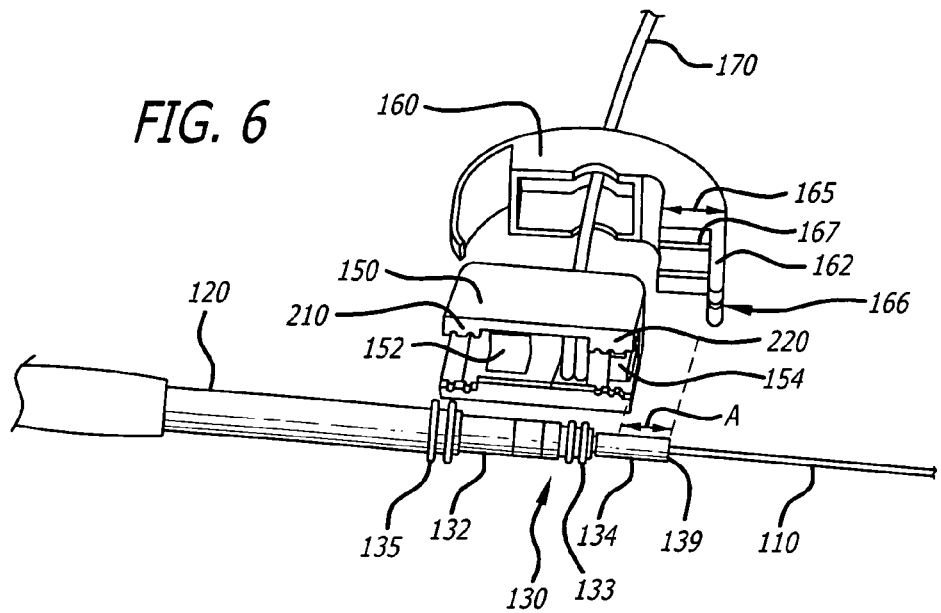
FIG. 6 is an exploded view of the invention, a lead connector, and an implantable pacing lead.
Figure 7:
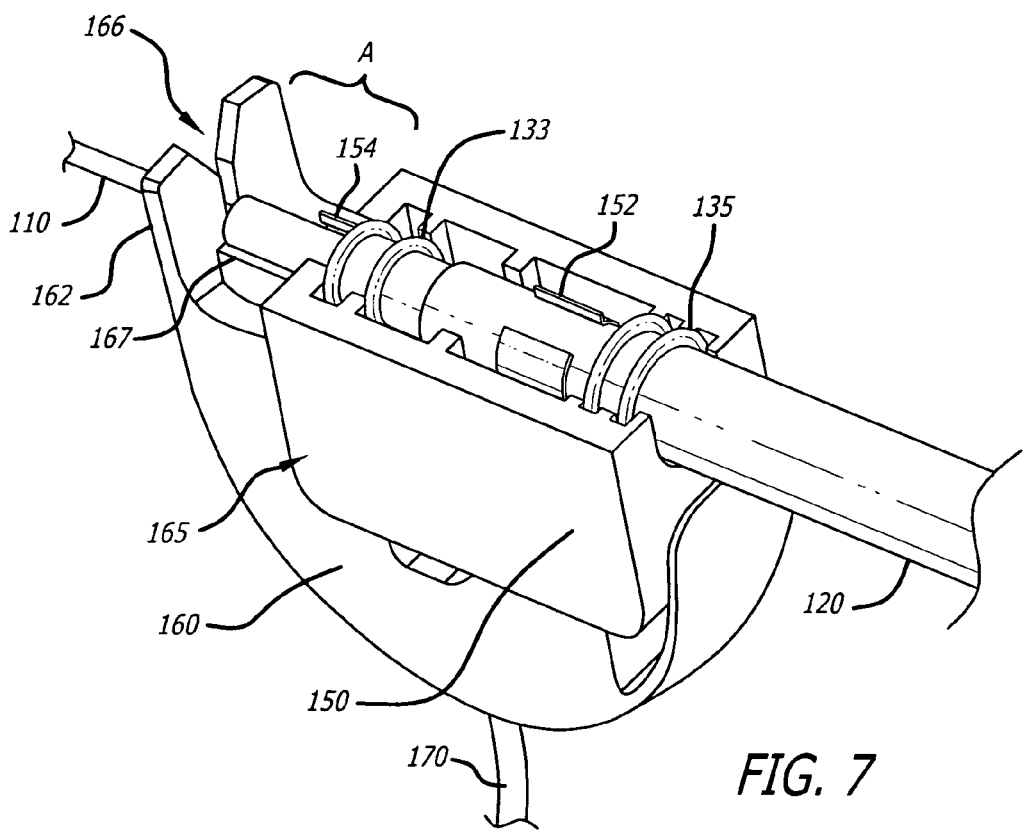
FIG. 7 is an exploded view of the grip having been slid down the twist tolerant cable and onto the low-profile adapter to form a single assembly.

FIGS. 4-8 depict the invention, which connects pacemaker analyzer 196 to pacing lead 120. In FIG. 4, the adapter assembly 165 attaches to the proximal end 122 of pacemaker lead 120. FIGS. 6 and 7 depict the low-profile adapter body 150 and grip 160, and how the lead connector 130 is secured to adapter body 150 with adapter clip contacts 152, 154. The adapter assembly 165 consists of a small body 150 and an attached larger grip 160, allowing an easier finger grip of the adapter. Both pieces are preferably made from medical grade plastic. The adapter body 150 and grip 160 releasably engage to form adapter assembly 165. This allows the pacing lead with the small adapter attached to be gripped and twisted without the adapter getting stuck in the hand or being brushed off the lead. The adapter assembly 165 is mounted on distal end 172 of twist-tolerant cable 170 while its proximal end 174 attaches to an electrical receptacle 180 or other type of electrical connector for connecting to equipment such as pacemaker analyzer 196. FIG. 6 shows how adapter body 150 with grip 160 removed is constructed to have a low profile so as to protrude less than approximately 3 pacing lead diameters above the lead connector. For example, if the ordinary lead diameter is approximately 3.5 mm, then preferably the low profile is less than about 3×3.5 mm =11.5 mm.

Figure 8:
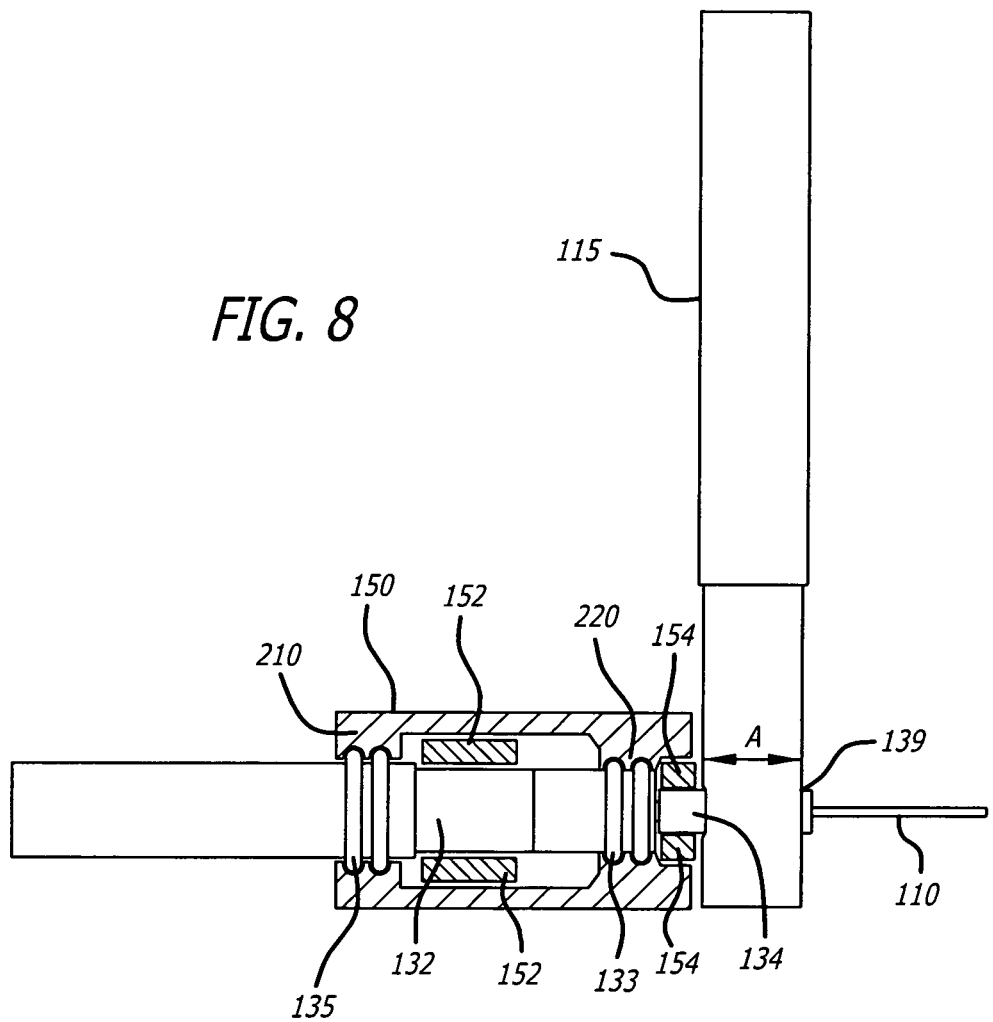
FIG. 8 is an elevation view of the adapter assembled on an IS-1 connector, including the torque wrench for rotating the tip end of the lead connector electrode.

FIGS. 6-8 show in detail how adapter assembly 165 is connected to lead connector 130. Lead connector 130 is, in this example, an IS-1 connector with cylindrical contacts 132, 134. Guide arm 162 of grip 160 helps to align adapter along the lead connector 130. The guide arm 162 includes slot or notch 166 to accommodate a stylet and includes flanges 167 on the inside of the arm for setting the required standoff of the adapter from the lead connector during attachment.

Attaching the Adapter Body and Grip to the Pacing Lead

To attach adapter assembly 165 to the lead, the physician first aligns the assembly parallel to and above lead connector 130 with stylet 110 inserted, as in FIG. 6, and then tilts guide arm 162 of grip 160 towards the lead connector 130. He then pushes stylet slot 166 over the stylet 110 and then slides guide arm 162 towards lead 130 until it abuts against the proximal end 139 of connector 130. In the absence of a stylet, guide arm 162 has flanges 167 on the inside that locate it correctly onto proximal end 139. This procedure precisely aligns the contacts 152, 154 in adapter body 150 with cylindrical contacts 132 and 134 of lead connector 130 respectively. The physician then pushes the rest of adapter assembly 165 onto lead connector 130, which snaps first the smaller clip contact 154 onto lead connector contact 134 (i.e., onto the narrower tip cylindrical contact on an IS-1) and then snaps clip contact 152 onto lead connector contact 132.

Note that the adapter assembly 165 cannot be connected with incorrect orientation because of the different diameters of the two contact pairs 152, 132 and 154, 134. Correct orientation is, however, facilitated by the adapter's guide arm 162, which makes correct orientation readily apparent. Also, the outer part of the grip 160 may be marked, or shaped to indicate the correct orientation. For example, it could be wider at the distal end and narrower at the proximal end. In addition, adapter body 150 could have orientation marking or shaping for instances when it is positioned on the pacemaker lead connector 130 without grip 160 in place. Further, the receptacle 180 could also be marked, so that the electrical contacts are identified with the corresponding lead connector electrodes.

Other embodiments of the device could combine the alignment and placement features of the grip 160 and the adapter body 150 into one part. For example, guide arm 162 could be integral with the adapter 150; it could be hinged; or, it could be designed to snap off, once alignment on the pacemaker lead had been achieved.

The Adapter Body on the Lead

Once adapter 165 is connected to lead connector 130, grip 160 can be removed. The design of grip 160 allows it to be gently twisted off the adapter body 150 (removal not shown). Grip 160 is then slid along cable 170 away from the adapter body 150, which remains attached to lead connector 130 by clip contacts 152, 154. In the case of an IS-1 lead connector, the ridges and valleys of stops 210, 220 in adapter body 150 interlock with sealing rings 133, 135 on the pacing lead connector 130. These features prevent adapter body 150 from sliding along its longitudinal axis off lead connector 130.

The present invention includes flexible lead connector holders, which in the preferred embodiment are clip contacts 152, 154 that have a spring force that releasably retains or holds lead connector 130. Clip contacts 152, 154 are preferably fabricated from a biocompatible, flexible, conductive metal such as surgical spring steel such as PH17. The clip contacts are approximately 0.2 mm to 0.3 mm thick. They are shaped into partially open tubes with diameters of approximately 2.65 and 1.6 mm and openings of approximately 2.1 mm and 0.95 mm. The preceding dimensions correspond to contacts that will fit an IS-1 connector, with the smaller dimensions corresponding to the IS-1 tip electrode.

The contacts must securely hold lead connector 130 yet have a controlled breakaway force that permits the contacts 152 and 154 to snap off the lead connector contacts 132, 134 if excessive force is applied to the adapter. Such force, if transmitted to an implanted lead, and especially one that is actively fixated, could damage cardiac structures. The preferred breakaway force is approximately 300-400 gm or 3-4 Newtons. The amount of breakaway force is controlled by the design of the lead connector holders, which in the preferred embodiment are clip contacts 152, 154.

Contacts can alternatively be constructed from a shaped, spring metal wire such as nitinol or beryllium-copper alloy. Other configurations with other metal contacts can perform the same function. For example, the sheet metal contacts could be configured as a set of three leaves or fingers so that electrical contact is made at a number of points. In the preferred embodiment of the invention, contacts 152, 154 perform the dual function of releasably retaining or holding lead connector 130 in adapter 150 while also providing electrical contact to maintain a continuous electrical signal. Other embodiments of the invention also exist. For example, contacts 152, 154 could simply be lead connector holders made of plastic or some other flexible material and located differently than shown. Meanwhile additional electrical contacts, separate from the structure that is releasably retaining lead connector 130, could provide the necessary conductivity for the electrical signals.

FIGS. 5-8 demonstrate an additional advantage of the present invention in relation to active fixation leads. FIG. 6 shows how contact 154 in adapter body 150 is narrower than contact 152 and is located flush with edge of adapter body 150, leaving a portion (width "A") of the lead connector's proximal tip contact 134 uncovered. This configuration permits access with a small torque wrench 115, typically supplied-in kits with active fixation leads, for rotating the tip contact to screw distal tip electrode 124 (see FIG. 4, corkscrew tip not shown) of lead 120 into the heart. For the first time in clinical practice this allows the continuous monitoring of a cardiac electrogram while the physician screws in the tip of an actively fixated lead. This improvement will avoid unnecessary heart trauma from a full deployment of the fixing corkscrew, about 10 to 12 turns, if electrical characteristics are unacceptable after the first turn. In the case of a rotating active lead, it should be emphasized that metal contact 154 must maintain good electrical contact with, but not exert excessive force or friction on, the lead connector. Otherwise continuous manipulation could be impeded or the lead contact could be scratched.

The electrical spring contacts are designed of steel or other material soft enough and formed without sharp edges, thus preventing damage to the pacemaker lead contacts. Without scratching, scoring, or scraping metal from the pacemaker leads, no residue will occur, metallic or otherwise. In addition, matching ridges and valleys of stops 210, 220 inside adapter body 150 protect the outer jacket and sealing rings of the pacemaker.

The invention works equally well for unipolar and bipolar lead connectors. In the former case, one contact is electrically inactive. As those of skill in the art will appreciate, the invention is not necessarily limited to IS-1 connectors, and could easily be adapted to other connectors. The adaptation to other pacemaker connectors could be in the form of a different size for each type of pacemaker connector or a single device with a range of fittings to allow it to be used with a number of different pacemaker connector sizes.

FIG. 4 includes another significant feature of the present invention: the twist-tolerant connecting cable 170 which uses a thin, floppy cable or wire to allow unimpeded manipulation of pacing lead 120. The preferred thickness of the cable is on the order of 1.5-2.5 millimeters, with a PVC jacket and a preferred length of about 1.5 meters. The cable should be long enough, thin enough, and flexible enough to allow manipulation of the implantable lead while readily absorbing the twisting caused by the rotation of the lead-connector assembly. At the same time the cable should not apply more than a minimal torque to the connection between the lead and the IS-1 connector, and preferably it should not be so long that it easily drags on the floor. Cable length, however, could reasonably vary from 1 to 2 or more meters, depending on the set-up in the implanting laboratory. The conductors in 170 should not be too thin, which would add significant resistance to the electrical circuit. Cable construction may employ two parallel or twisted pair of 28-32 AWG conductors with a tough but thin, pliable insulation jacket. A PVC jacket is preferred, because silicone rubber is typically not robust enough. PET and Teflon are stiffer than the PVC, and therefore less desirable.

Other Aspects of the Invention

Those of skill in the art will understand and appreciate that variations of the present invention can be made without departing from the spirit and scope of the claims. For example, in the preferred embodiment grip 160 is permanently attached to cable 170 so grip 160 slides between clip 150 and receptacle 180. The invention, however, should not be so limited. While different manufacturers of pacemaker analyzers have different sockets for accepting cables, most are equipped with cables terminated with alligator clips, such as alligator clips 192, 194 that would connect to receptacle 180. Here, too, the invention should not be limited to what is described. Twist-tolerant cable 170 could be configured to connect directly to an electrical device like a pacemaker analyzer, or even to connect wirelessly. If the invention is configured to include a connection at distal end 174 of cable 170, the connection need not be limited to the electrical receptacle 180 or the alligator clips 192, 194.

One preferred embodiment of the invention may be supplied as an inexpensive, sterilized, and disposable unit for single use. During normal use, assembly 165 and twist tolerant cable 170 remain in the sterile field. Receptacle 180 may be non-sterile, and alligator clips 192, 194 and wires 197, 198 need not be sterilized. It is intended, however, that the scope of the invention cover a device in which some, all, or none of the invention is reusable.

In another configuration the invention or some components of the invention could be pre-connected and pre-packaged together with the pacemaker lead. Furthermore, this invention is not limited to permanent pacemaker leads. It can also be potentially utilized with the leads used with temporary pacemakers or indeed any electrical lead placed within the body for either therapeutic or diagnostic use.

Figure 1:
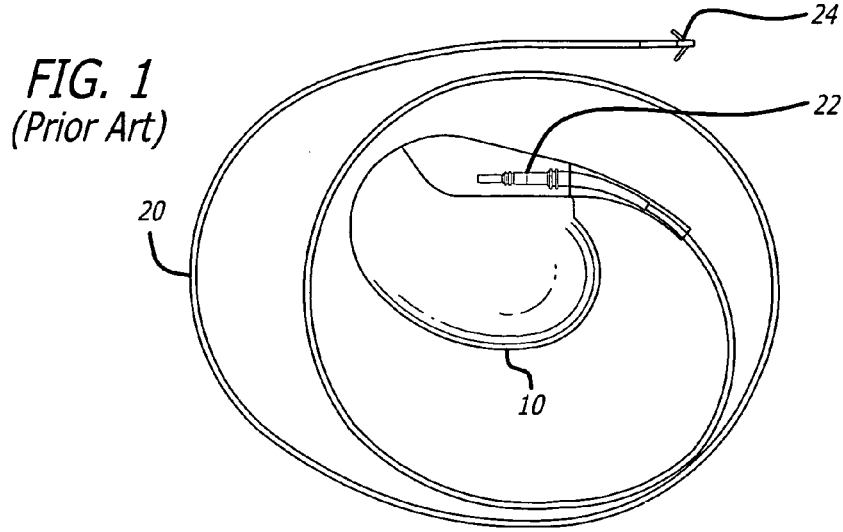
FIG. 1 is a drawing of a prior art pacemaker and an implantable pacemaker lead.
Figure 2:
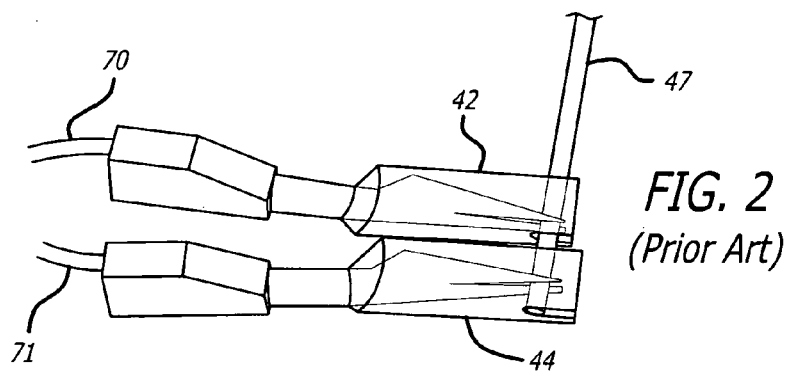
FIG. 2 is a drawing of prior art alligator clips.
Figure 3:
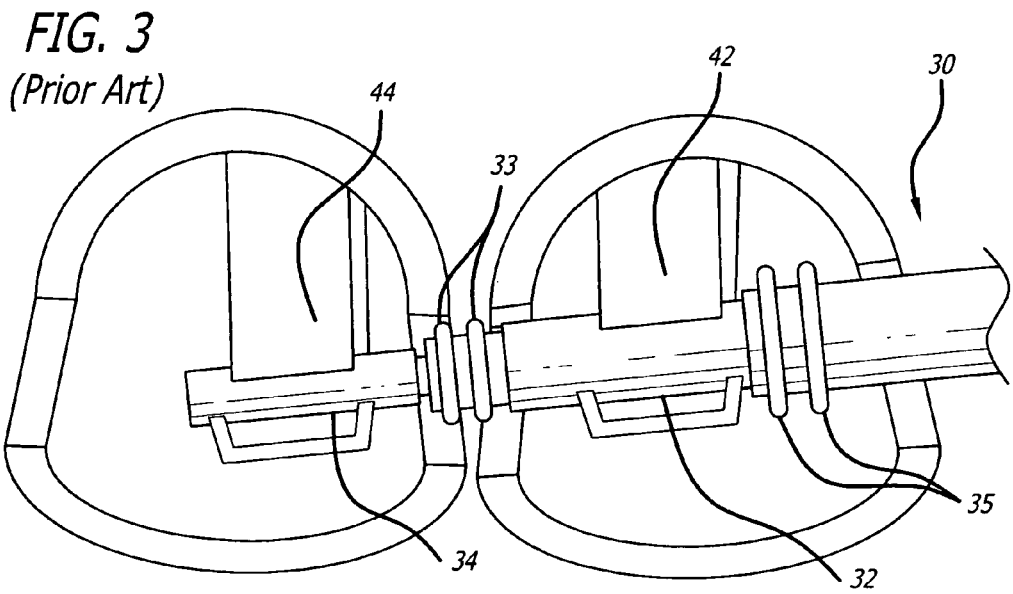
FIG. 3 is a drawing of prior art alligator clips attached to the electrodes of an IS-1 lead connector.

Terms such as lead, electrode, contact, and connector sometimes have different or overlapping meanings to physicians, equipment designers, and others of ordinary skill in the art. The meaning will sometimes depend on the context in which those terms are used. For example, contacts 132, 134 of lead connector 130 may also be referred to as electrodes or electrode contacts. Similarly, contacts 152, 154 may be referred to as contacts, clips, springs, electrodes, or connector holders, depending upon the context. Terms such as connected can have a broad meaning. For example, in FIG. 2 alligator clips are directly connected (mechanically and electrically) to wire or electrode 47. In FIG. 5, pacemaker analyzer 196 is connected (electrically but not mechanically) to pacing lead 120. In clinical practice, lead connector 130 is sometimes referred to simply as the lead. It will be clear to those of skill in the art how those terms are used in the art and in the present context to describe the invention.

While the present invention has been described in conjunction with specific, preferred embodiments, it will be evident to those of skill in the art that alternatives, modifications, and variations of the invention are possible. Therefore, it is contemplated that the appended claims will embrace any such alternatives, modifications, and variations of the invention, which will fall within the spirit and scope of the claims.

What is claimed is:

1. A device for connecting an implantable electrical lead and lead connector to an external electrical information analyzer, comprising:
   a low profile adapter body, including a shrouded housing with an open end;
   two, thin, flexible holders for physicall engaging the lead connector, wherein the lead connector holders are disposed in the adapter body, are accessible through the open end of the shrouded housing, have ends generally flush with the open end of the shrouded housing, and have defined breakaway forces such that an excessive force applied to the electrical lead will cause the lead connector to disengage from the lead connector holders;

a light and twistable cable for connecting the adapter body to the external electrical information analyzer, wherein the cable is sufficiently light and twistable to permit easy manipulation, including rotation, of the electrical lead while the cable is connected to the lead connector and the external electrical information analyzer; and, a grip having an open end and slidably disposed on the light and twistable cable in a direction generally perpendicular to the lead connector, wherein the grip is configured to receive the shrouded housing at the open end to form a unitary assembly with the adapter body and is also configured to be releasably engageable with the adapter body to facilitate manipulation of the adapter body.

2. The invention of claim 1, wherein the light and twistable cable has a thickness of approximately 1.5 to 2.5 millimeters.

3. The invention of claim 1, wherein the first and second lead connectors have a breakaway force on the order of three to four Newtons.

4. The invention of claim 1, wherein the adapter body has a thickness on the order of three to four diameters of a cardiac pacing lead.

5. The invention of claim 1, wherein the adapter body includes a stop to prevent the lead from sliding along its longitudinal axis.

6. The invention of claim 1 further comprising a notch in the grip, wherein the notch is configured to align the lead connector in the adapter body when the lead connector is connected to a stylet.

7. The invention of claim 1, wherein the lead connector holders physically engage and electrically connect to the lead connector.

\* \* \* \* \*